United States Patent [19]

Mojtabaj

[11] Patent Number: 5,044,308

[45] Date of Patent: Sep. 3, 1991

[54] DEVICE AND METHOD FOR FLUORESCENCE MICROSCOPIC CONTROLLED FORMATION OF MONOMOLECULAR LAYERS OF ORGANIC FILMS

[76] Inventor: Fatemeh Mojtabaj, 3570 Greenbrier Blvd. #408C, Ann Arbor, Mich. 48105

[21] Appl. No.: 378,460

[22] Filed: Jul. 10, 1989

Related U.S. Application Data

[63] Continuation of Ser. No. 157,846, Feb. 18, 1988, abandoned.

[51] Int. Cl.$^5$ .............................................. B05C 3/02
[52] U.S. Cl. .................................. 118/402; 118/403; 118/429
[58] Field of Search ........................ 118/402, 403, 429; 220/81 R, 614

[56] References Cited

U.S. PATENT DOCUMENTS

| | | | |
|---|---|---|---|
| 2,385,954 | 10/1945 | Tarnopol | 220/81 R |
| 4,599,969 | 7/1986 | Barraud et al. | 118/429 |
| 4,643,125 | 2/1987 | Barlow et al. | 118/402 |

OTHER PUBLICATIONS

Fromherz, P., "Instrumentation for Handling Monomolecular Films at an Air-Water Interface," Rev. Sci. Instrum., vol. 46, No. 10, 1380-1385 (1975).
Hänggi-Mojtabai, F., "Total Internal Reflection and Fluorescence Recovery. . . Membranes," Doctoral Thesis Submitted to the School of Natural Science, University of Basel, Switzerland, Jun. 26, 1985.
Reprint from Materials Engineering entitled "Perfluoroelastomers Seal in Hostile Enivoronments", No. E-36434 10M, Cleveland, Ohio, Penton Publishing, Inc., Oct. 1986, 2 pages.
"Kalrez Perfluoroelastomerm Parts—Physical Properties and Compound Comparisons", DuPont Publication BMP-10003, Jan. 1987, 2 pages.
"Kalrez Perfluoroelastomer Parts—Prolong the Life of Control Seals and Rubber Components with Kalrez", DuPont Publication E-33820 091-79, 8 pages.
"Kalrez Perfluoroelastomer Parts—Seal Design Guide," Dupont Publication E-33808, Mar. 5, 1984, 5 pages.
"Kalrez Perfluoroelastomer Parts—Technical Information", DuPont Publication E-69557 (undated), 2 pages.
"Kalrez Perfluoroelastomer Parts—Physical Properties and Compound Comparisons", DuPont Publication E-33806, Jan. 1980, 2 pages.
"Kalrez Perfluoroelastomer Parts—Chemical and Fluid Resistance", DuPont Publication E-42789, Mar. 1984, 15 pages.
"Kalrez Perfluoroelastomer Parts—Superior Sealing Performance Under Demanding Service Conditions", DuPont Publication (undated), 5 pages.
"The Kalrez Advantage", DuPont Publications (undated), 1 page.
B. Pethica, "Experimental Criteria for Monolayer Studies . . . ", Paper Presented at a Workshop on the Molecular Engineering of Ultrathin Polymeric Films, Davis, CA, Feb. 18-20, 1987.
Weis and McConnell, "Cholesteral Stabilizes the Crystal-Liquid Interface . . . ", J. Phys. Chem., 1985, pp. 4453-4459.

*Primary Examiner*—Evan Lawrence
*Attorney, Agent, or Firm*—Cohen, Pontani & Lieberman

[57] ABSTRACT

A trough for the formation of a monomolecular layer of an organic film on a frame preferably having top and bottom separable frame portions. A plate is disposed within the frame and is formed of a rigid substance. A sealing element of chemically inert material is positioned between the top of the plate and the top frame portion and preferably comprises a perfluoroelastomeric material that is conformable to the top of the plate and to the top frame portion to prevent subphase leakage from the trough. Apparatus is provided for laterally compressing a layer of amphipilic solution deposited on the subphase to form a solid monomolecular film. The apparatus includes a movable barrier dimensioned to rest to superposed relation on the plate. An additional sealing element of chemically inert material may be spaced adjacent to the above-mentioned sealing element, and also positioned between the top of the plate and the top frame portion for cooperating with the above-mentioned sealing element to prevent the subphase from reaching the frame.

45 Claims, 2 Drawing Sheets

DEVICE AND METHOD FOR FLUORESCENCE MICROSCOPIC CONTROLLED FORMATION OF MONOMOLECULAR LAYERS OF ORGANIC FILMS

This is a continuation of application Ser. No. 07/157,846 filed Feb. 18, 1988, now abandoned.

FIELD OF THE INVENTION

This invention relates to a device and method for preparation of microscopic visualization of monomolecular layers of organic films at an air-water interface and on solid supports, and to a novel design of a leak-free barrier assembly for mounting on monolayer troughs.

BACKGROUND

In biology, monolayers of amphiphilic molecules have long been used as well defined model systems of cell membranes. In recent years, however, the interest in ultrathin organic films has dramatically increased due to their potential applications in the microelectronic industry and in the biotechnology industry. These applications call for decreased film thickness than heretofore available. Thus, improved and carefully engineered instruments are necessary for the fabrication of ultrathin films with high degree of structural order and well defined characteristics.

Historically, monomolecular films at the air-water interface are produced by using a Langmuir trough (I. Langmuir, J. Am. Chem. Soc. vol. 39, 1848, (1917)). The trough, a special form of container, is filled with a subphase, usually highly purified water. A dilute solution of an amphiphilic molecule is dissolved in a volatile solvent and is deposited on the subphase. As the solvent evaporates, a monomolecular layer of the amphiphile spreads over the surface of the subphase. This thin, quasi two-dimensional film is then compressed laterally by means of a barrier to form a solid monomolecular film. Supported planar monomolecular or multimolecular layers (monolayers or multilayers) can then be prepared by transferring the floating monolayer onto a solid substrate. The transfer is usually accomplished by use of the Langmuir-Blodgett technique (K. B. Blodgett, J. Am. Chem. Soc., vol. 57, 1007 (1935)). These supported planar membranes, called Langmuir-Blodgett films are known for their high quality and well-organized structure. However, defects in these films are present, since the commercial instruments that are currently used for their preparation are inadequate for the characterization of the physical state of the membrane prior to the transfer stage.

Recently the technique of fluorescence microscopy has been applied toward the problem of determining the structure and properties of monolayers (Peters R. and Beck K., Proc. Natl. Acad. Sci. USA, vol. 80, 7183 (1983)). In this method, the monolayer can be directly visualized at the air-water interface through a microscope objective. The technique is comprised of a specially designed monolayer trough that is positioned on the stage of a fluorescence microscope equipped with the epi-illumination technique, where a light source (e.g. a laser or lamp) excites certain fluorescent probes within the monolayer. The emitted fluorescence is then observed through the microscope objective. In order to observe the monolayer, a small amount (less than 1%) of a fluorescent amphophilic dye is mixed with the monolayer forming compound.

Fluorescence microscopic analysis of the monolayers at the air-water interface and at solid supports, has revealed that the structure and order in these ultrathin films are strongly influenced by a variety of factors that can be easily controlled for the production of films free of defects. For example, changes in temperature, surface pressure, the degree of impurities in the subphase or in the film, or the nature of the solid support itself, can alter the structure and properties of certain monolayers. (Losche M. and Mohwald H., Eur. Biophys. J., vol 11, 35, (1984); Weis R. M. and McConnell H. M., J. Phys. Chem., vol. 89, 4453 (1985); Suel M., Subramaniam S., and McConnell H. M., J. Phys. Chem., vol. 89, 3592, (1985)).

Prior to the development of this invention, there were no commercially available monolayer troughs that were suitable for fluorescence microscopy of monolayers at an air-water interface. Flow and convection of the subphase in conventional monolayer troughs disrupt visualization of the monolayer using the fluorescence microscopy technique. Carefully engineered instrumentation is necessary to overcome this problem. Moreover, due to the smaller size of the microscope troughs, the problem of leakage around the trough barriers is a far more serious problem than in the larger scale Langmuir troughs.

A number of fluorescence microscope troughs have been developed in research laboratories (Peters R. and Beck K., ibid; Losche M. and Mohwald H. Rev. Sci. Instrum. vol. 55, 1968 (1984); McConnell H. M., Tamm L. K., and Weis R. M., Proc. Natl. Acad. Sci. USA, vol 81, 3249, (1984); and Gaub H. E., Moy V. T., McConnell H. M., J. Phys. Chem. vol 90, 1721 (1986). These troughs were designed for specific applications, and their use is limited to the technology available in those laboratories. Thus, due to their lack of versatility, they are not feasible for commercial exploitation. For example, the Losche and Mohwald trough is too costly because it is permanently cemented to the microscope objective. The Peters and Beck trough and the McConnell et al. trough can only be used on upright microscopes.

SUMMARY OF THE INVENTION

Accordingly, there is a need for a fluorescence microscope trough that is versatile, inexpensive, easy to use, and can be easily adapted for use with inverted and upright microscopes. The trough of the present invention fulfills that need.

For example, the trough of the present invention can be easily adapted onto the stage of any inverted as well as upright microscope providing a versatility not heretofore available. The trough of the present invention is thus compatible with two illumination techniques; i.e., epi- and Total Internal Reflection (TIR) illumination. By selectively illuminating preferred regions of the specimen, the latter technique is an advanced method of illumination that is becoming of increasing interest in many applications.

In order to reduce convective motion, the depth of water in monolayer troughs must be as low as possible. Prior art microscope troughs are constructed from Teflon, which due to its hydrophobic character requires that the depth of water in the trough be at least 3-4 mm. For this reason, additional devices have been necessary in prior art troughs to suppress convection in the troughs. These devices are not easy to operate, limit the observational area and can cause possible edge effects.

In contrast to prior art devices, the present invention requires no additional devices in order to suppress the flow of water in the trough. The present invention provides that the bottom of the trough be constructed from a hydrophilic material, preferably fused silica. Due to the lower contact angle between silica and water, the depth of water can be easily reduced to less than 0.5 mm in this trough, obviating the need for additional devices to suppress flow. Due to minimized fluctuations in the subphase, distinct features of the monolayer can be observed over periods of hours. This feature which is not easily possible in the prior art is necessary for the applications where long times are necessary to observe the monolayer in equilibrium.

The lower depth of water has the additional advantage that high power, high numerical aperture objectives with high light collection efficiency can be successfully utilized even with the inverted microscope. High power, high numerical aperture objectives have a shorter working distance which is compensated for by using a shallower depth of water and a thin glass plate in this invention. Thus resolutions of better than 0.7 $\mu$m are possible with this invention for the detection of minute structures which were not previously observable with the trough introduced by Losche and Mohwald for inverted microscopes (see Losche M. and Mohwald H. Ibid and Eur. Biophysical J., vol. 11, 35–42, (1984)). In an up-right microscope since the objective can be at the close vicinity of the monolayer, the depth of water does not impose a restriction on the use of objectives with high numerical aperture and shorter working distance. However, with the up-right microscope troughs as well as with the inverted microscope troughs, the higher depth of water interferes with the observation of the monolayer due to increased fluctuations that are transferred to the monolayer from the subphase as discussed earlier. Therefore, keeping the depth of water to a minimum is of extreme advantage in all microscope monolayer troughs, and has been successfully achieved in this invention.

The present invention also allows for scanning of the entire area of the monolayer and minimizes possible edge effects and allows for conventional focusing by vertical motion of the microscope stage or objective, rather than by careful adjustment of the water level to the objective's focal plane as is required in some other prior art devices.

Additionally, the trough of the present invention is easily demountable for cleaning, overcomes the problem of leakage around the barriers of the trough. Supported planar membranes can be prepared on both hydrophilic and hydrophobic supports. The unique design of this invention allows for the visualization of the structure of the monolayer prior to and immediately after the transfer onto the solid support. This feature which facilitates the preparation of supported films free of defect, is not available with the prior art troughs. In this trough, all surfaces coming into contact with any of the components that make up a working interface are constructed from chemically inert materials that are free of surface active components. By chemical inertness, we mean that these compounds can be in continuous contact with another substance (e.g., the subphase, the film, or the organic solvents that are typically used during the film preparation) with no detectable chemical reaction taking place. Lastly, appropriate functional groups, e.g. enzymes and proteins can be easily attached to the membrane for specific uses in biology and biotechnology using the trough of the present invention.

Accordingly, a trough for the formation of monomolecular layers of organic films on a subphase is provided having a frame with an inner rim portion, and outer rim portion surrounding the inner rim portion, a plate, disposed within the frame, made of a rigid inert, transparent, non-fluorescent, hydrophilic substance and having a central aperture, and means extending through the aperture for securing the plate and locating it with respect to a barrier. In this use, nonfluorescent means (1) that the material does not exhibit any fluorescent properties or (2) that the material's fluorescence does not interfere with the fluorescence of the monolayer forming compounds or other compounds of interest for visualization in the trough. Also provided are hydrophobic sealing means positioned between the top of the plate and the securing and locating means and frame and formed to prevent liquid leakage out of the trough, hydrophobic spacer means positioned between the bottom of the plate and the frame and securing and locating means and formed to prevent direct contact between the plate and the frame and securing and locating means, barriers of a flexible, resilient, inert, hydrophobic material, axially dimensioned to rest in superposed relation on the plate and barrier rotation means for rotating the barrier about the vertical axis of the securing and locating means.

In one embodiment, the securing and locating means is a pair of discs, having mating threaded end portions and opposed ledges which form a groove dimensioned to receive the plate when the end portions are threaded together, the hydrophobic sealing means is a pair of rings disposed between the top of the plate and one wall of the groove and the hydrophobic spacer means is a pair of rings disposed between the bottom of the plate and the other wall of the groove. Both pairs of rings are preferably made from the perfluoroelastomer sold under the brand name Kalrez by E. I. Du Pont de Nemours Company. They may also be made of fluorocarbon resin polymers such as Teflon FEP, a brand of resin polymer also marketed by Du Pont.

DETAILED DESCRIPTION OF THE PREFERRED EMBODIMENTS

Figure 2:
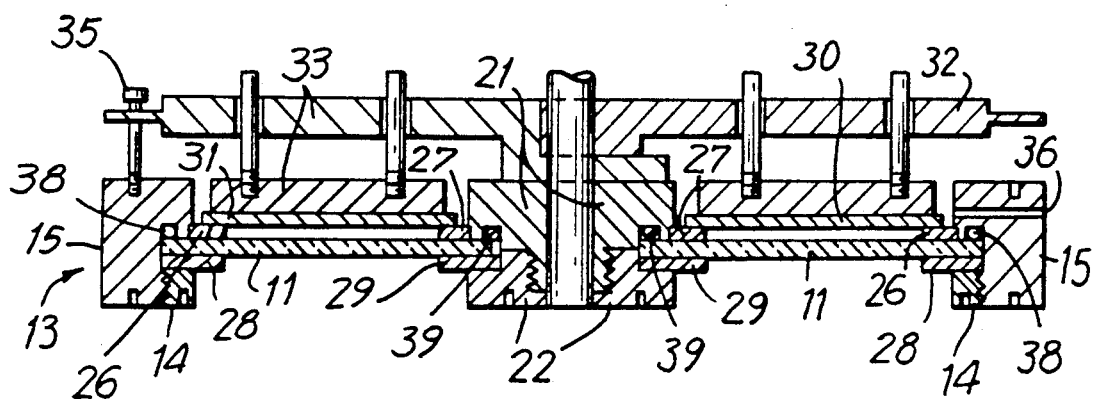
FIG. 2 is a cross-sectional view of FIG. 1, taken along the line 2—2.
Figure 1:
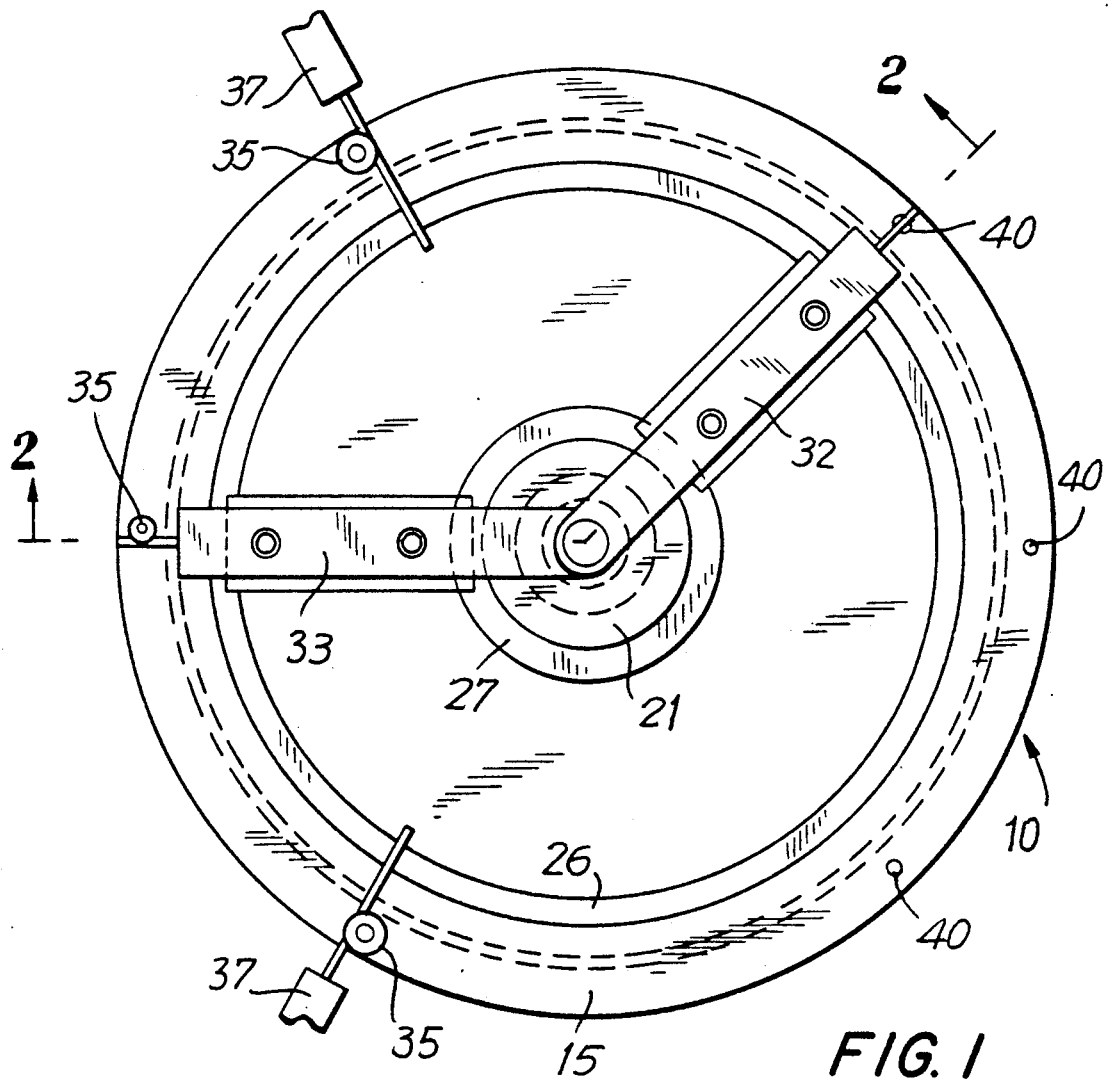
FIG. 1 is a plan view of the device of the present invention.
Figure 3:
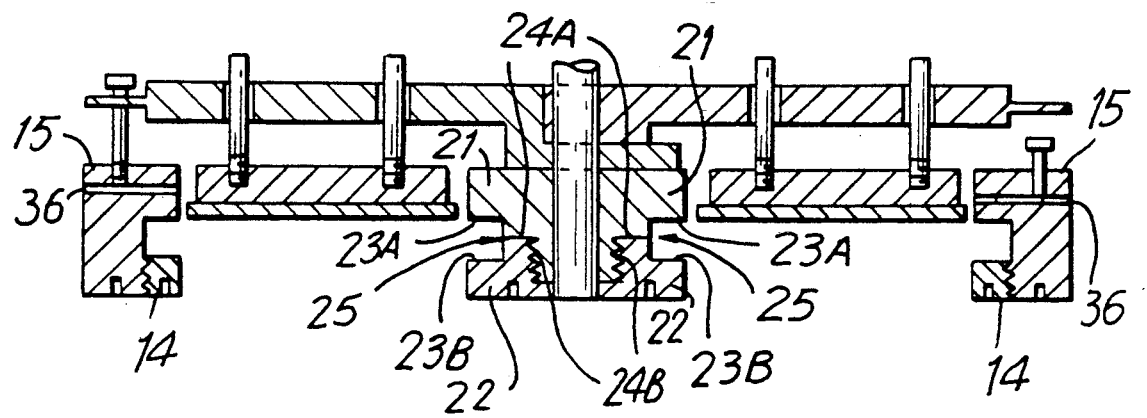
FIG. 3 is a view of FIG. 2 showing partial assembly of a preferred embodiment of the present invention.

Referring to FIGS. 1 and 3 there is generally disclosed a circular trough 10, having a plate 11 with a centrally located aperture, 12. Plate 11 is positioned in stainless steel frame 13 which is formed from inner and outer rims 14 and 15 respectively which screw together as illustrated in FIG. 2. Preferably plate 11 is made from fused silica. Securing and locating means 21 and 22 extend through aperture 12 of plate 11 for securing the plate and locating it with respect to a barrier 30 (discussed below). As best shown in FIG. 2, securing and locating means 21 and 22 comprise a pair of discs having opposed ledges 23A and 23B and mating threaded end portions 24A and 24B. Ledges 23A and 23B form a groove, 25, dimensioned to receive plate 11 when end portions 24A and 24B are threaded together.

Hydrophobic sealing means 26 and 27 are positioned between the top of plate 11 and securing and locating means and formed to prevent liquid and monolayer leakage out of trough 10. Such hydrophobic sealing means 26 and 27 comprises a first pair of rings. Rings 26 and 27, on the top side of trough 10 provide a seal against leakage of the subphase and the monolayer from inner and outer rims 14 and 15. They also act as a hydrophobic base for the diagonal traverse of the barriers over the subphase. Thus, they should be level and coplanar. Although Teflon FEP is adequate, rings made of synthetic perfluoroelastomer resin sold under the trade designation "Kalrez" are preferred. Kalrez is a cross-linked rubber which compresses easily and seals effectively on all types of surfaces. Kalrez parts are the only elastomer that match Teflon PTFE in chemical resistance. But unlike Teflon, Kalrez parts have the true rubber properties that are vital to sealing applications. Hydrophobic sealing means 26 and 27 provide a hydrophobic rim that is level and coplanar on which the hydrophobic barriers traverse without leakage. The hydrophobic rim also provides a base for positioning the solid support (for the preparation of supported planar membranes) and the TIR block (for the TIR illumination technique).

Also provided are hydrophobic spacer means 28 and 29 positioned between the bottom of plate 11 and, respectively, frame 13 and element 22 of the securing and locating means 22, for preventing direct contact between plate 11 and frame 13 and the securing and locating means. Preferably hydrophobic spacer means 28 and 29 comprises a second pair of Kalrez rings. Teflon FEP is an adequate alternative compound to be utilized.

Figure 4:
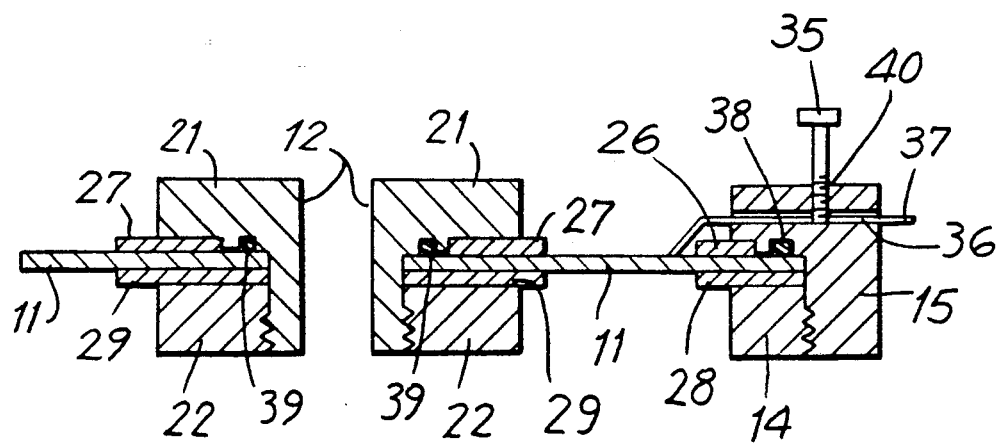
FIG. 4 is a partial cross-sectional view of FIG. 1 showing another preferred embodiment of the present invention.

Preferably, as shown in FIGS. 2 and 4, a pair of hydrophobic sealing ruigs 38 and 39 is additionally provided in order to optimize the sealing ability against subphase leakage and ensure that the component parts may be cleaned quickly and completely. One of the pair is disposed within the inner circumference of frame 13, the other of the pair is disposed within the outer circumference of securing and locating means 21. Sealing ruigs 38 and 39 comprise O-rings made preferably from Kalrez. Kalrez O-rings have the true rubber properties of elasticity and recovery that are vital to sealing applications. They easily conform to the irregular metal and glass surfaces and are easy to install and replace. Due to these characteristics, the trough can be easily assembled, with applying minimal pressure on the glass plate, thus reducing the risks of glass breakage and increasing time and cost efficiency. FIG. 4 shows the device of the present invention, with sealing ruigs 38 and 39, an economical alternative embodiment.

For use with an inverted microscope (where the monolayer is viewed from the bottom of the trough), the depth of water plus the thickness of plate 11 should not exceed the working distance of the objective. It is practical to choose the thickness of sealing means 26 and 27 to substantially match the required depth of water. For example, for a 40 power objective with a 1.5 mm working distance, a 1 mm thick fused silica plate is combined with 0.5 mm thick sealing means (26 and 27).

Two radial barriers 30 and 31 respectively divide the water surface into two compartments. Barrier 30 driven by a motor drive (not shown) is used to compress the monolayer on the water surface. Barrier 31 is usually kept fixed by means of stop 35. Barriers 30 and 31 are made of flexible, resilient, inert hydrophobic material, axially dimensioned to rest in superposed relation on plate 11. In its preferred embodiment, the barriers are either Teflon or Kalrez. Teflon PTFE is a chemically inert hydrophobic resin, but fairly rigid. Thus by not conforming to the edges of the troughs, monolayer leakage around the sides of Teflon barriers is a general problem in most monolayer troughs. In this invention, we introduce the use of Kalrez perfluoroelastomer sheets (manufactured by Du Pont) as an ideal seal for barrier assemblies against monolayer leakage around the sides of the barriers. Kalrez is a cross-linked rubber which compresses easily and by conforming to irregular surfaces seals effectively on all types of surfaces. Kalrez parts are the only elastomer components that match Teflon PTFE in chemical inertness.

In order to rotate barriers 30 and 31, barrier rotation means 32 and 33 are provided, for rotating the barriers about the vertical axis of securing and locating means 21 and 22 in order to compress or expand the surface area of the monolayer. Stop 35 attached to frame 11 is formed and positioned to engage with one of the barrier rotation means 33 to prevent further rotation of the same. Preferably stop 35 constitutes a screw, which fits into one of threaded holes 40 in the top of outer rim 15.

In operation the trough is disassembled for cleaning. Plate 11, the two hydrophobic sealing means 26 and 27 the pair of hydrophobic sealing ruigs, 38 and 39, and spacer means 28 and 29 are cleaned separately before each use by soaking in hot (70° C.) detergent for ½ hour. They are rinsed thoroughly under running distilled water for 2-3 hours, and dried in a 70° oven. For best results, plasma cleaning of plate 11 immediately before each application is also recommended.

After assembling the parts, trough 10 is placed in a holder (not shown), that is fixed on the micropscope stage by appropriate means, and on which a Wilhelmy balance (a device used to measure surface pressure) and motor drive for the barrier assembly is positioned. On an upright microscope, where the monolayer is viewed from the top, it is preferable to connect the motor to the barrier rotation means from the bottom of the trough. Trough 10 then is filled with a sufficient amount of subphase in order to avoid tearing of the water film during the film preparation (approximately a depth of 2-3 mm of the subphase is sufficient). In order to assure the cleanness of the subphase, radial barrier 30 is swept over the subphase. If no change in surface pressure is detected, the subphase can be used for the preparation of the monolayer. A small amount of the film forming compound, mixed with an appropriate fluorescent probe, dissolved in a volatile organic solvent is deposited on the surface by means of a syringe. After allowing sufficient time for the solvent to evaporate, trough 10 is covered by a plexiglass cover (not shown) in order to avoid dust and air convection.

The epi-illumination technique is used in order to observe the emitted fluorescence through the microscope objective. Depending on the objective working distance, the depth of water is adjusted to an approximate position, by draining the water, until the monolayer is visualized in the field of view. The depth of water is adjusted by use of stainless steel syringe 37 which is mounted on frame 13 through one of the ports 36. As shown in FIG. 4, the head of the syringe is ground so that it rests flat on plate 11. Stop 35, in the form of a screw, secures the syringe in place. Alternatively, syringe 37 may rest on the top portion of inner and outer rims 14 and 15, being removably secured in place by means of a housing (not shown) which is screwed onto outer rim 15 using stop 35, as already discussed. In this way, water can be eliminated from the lowest depths of water in trough 10 rather than from the surface. Fine focusing is achieved by conventional focusing through the vertical motion of the microscope objective or stage. The physical state of the monolayer can be changed, by compressing or expanding the monolayer with the moving radial barrier 30.

Additional syringes 37 can be positioned at other ports 36, around the trough for changing the subphase composition or injecting proteins or other functional groups into the subphase, as best seen in FIG. 1.

The monolayer formed upon compression or expansion can be adhered to hydrophobic substrates (e.g. alkylated glass plates, or pure metals such as gold, silver or germanium), through its hydrophobic tails, which are oriented towards the air and away from the surface of the substrate. In order to do this the depth of the subphase is slowly raised to a higher level (in order to avoid tearing of the subphase during the manipulation), and the substrate is placed horizontally over the monolayer. Visualization of the supported monolayer through the microscope objective is made possible by allowing the substrate to rest on the rims of the trough. With certain substrates, epi- as well as TIR illumination can be used for observation.

In the preparation using hydrophilic substrates, the monolayer is attached to a hydrophilic support (e.g. glass, $Al_2O_3$ or $CaF_2$), through its hydrophilic heads, which are oriented towards the subphase. A new method in formation of these monolayers is herein introduced. In this method, a thin sheet of the hydrophilic substrate is placed in the trough before film preparation (or the film is transferred over the substrate after preparation, with the help of the barriers). Water is drained slowly from a syringe placed in the monolayer-free region of the trough. The monolayer adheres to the substrate as the film of water between the monolayer and the substrate diminishes. Instead of draining, it is possible to allow the subphase to evaporate. In some applications, it is possible to take advantage of the hydrophilic nature of the bottom of the trough and adhere the monolayer directly to it, using the same procedure.

In both of the foregoing applications of this invention, functional groups like enzymes or proteins can be administered into the monolayer by known methods.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A trough for the formation of a monomolecular layer of an organic film on a subphase comprising:
   (a) a frame having an inner rim portion and an outer rim portion surrounding said inner rim portion;
   (b) a plate, disposed within said frame, of a rigid, chemically-inert, transparent, non-fluorescent, hydrophilic substance, and having a central aperture;
   (c) means, extending through said aperture, for securing said plate and locating it with respect to a barrier;
   (d) hydrophobic sealing means positioned between the top of said plate and said securing and locating means and said frame and formed to prevent subphase leakage from said trough;
   (e) hydrophobic spacer means positioned between the bottom of said plate and said frame and said securing and locating means and formed to prevent direct contact between said plate and said frame and said securing and locating means;
   (f) said barrier being of a flexible, resilient, chemically-inert, hydrophobic material, axially dimensioned to rest in superposed relation on said plate;
   (g) means for rotating said barrier about the vertical axis of said securing and locating means to laterally compress a layer of amphipilic solution deposited on said subphase to form said monomolecular layer; and
   (h) a pair of hydrophobic sealing rings, one ring disposed within the inner circumference of said frame, the other ring disposed within the outer circumference of said securing and locating means.

2. The trough of claim 1 wherein said securing and locating means comprises a pair of discs, having opposed ledges and mating threaded end portions, said ledges forming a groove dimensioned to receive said plate when said end portions are threaded together to secure said plate in said frame.

3. The trough of claim 2 wherein one of said pair of discs is formed to hold said barrier.

4. The trough of claim 1 wherein said frame comprises a pair of rims having opposed interior ledges and mating threaded end portions, said interior ledges forming an interior groove dimensioned to receive said plate and securing said plate in said frame, when said end portions are threaded together.

5. The trough of claim 4 wherein said frame has at least one port positioned to communicate with the interior of said frame below said organic film and dimensioned to receive a syringe.

6. The trough of claim 5 additionally comprising a syringe housing removably connected to said port.

7. The trough of claim 3 wherein said barrier rotation means comprises a pair of weighted arms mounted on said securing and locating means, at least one of said arms being rotatable about said vertical axis of said securing and locating means and wherein said barrier depends from said arms.

8. The trough of claim 1 wherein said barrier is formed from a perfluoroelastomer.

9. The trough of claim 1 wherein said hydrophobic sealing means positioned between the top of said plate and said frame comprises a first pair of rings disposed between the top of said plate and one wall of a groove dimensioned to receive said plate when said end portions are threaded together to secure said plate in said frame.

10. The trough of claim 1 wherein said hydrophobic spacer means comprises a second pair of rings disposed between the bottom of said plate and the other wall of aid groove.

11. The trough of claim 9 wherein said hydrophobic sealing means is selected from a group consisting of perfluoroelastomers and fluorocarbon resins.

12. The trough of claim 11 wherein said hydrophobic spacer means is selected from a group consisting of perfluoroelastomers and fluorocarbon resins.

13. The trough of claim 1 wherein said pair of hydrophobic sealing rings comprises a pair of O-rings made from a synthetic perfluoroelastomeric material.

14. A trough for the formation of a monomolecular layer of an organic film on a subphase, comprising:
   a frame having top and bottom separable frame portions;
   a plate disposed within said frame and formed of a rigid substance;
   first and second adjacently spaced sealing means of chemically-inert material positioned between the top of said plate and the top frame portion and cooperating with each other to prevent the subphase from reaching the frame; and
   means for laterally compressing a layer of amphipilic solution deposited on said subphase to form a solid monomolecular film, said means including a movable barrier dimensioned to rest in superposed relation on said plate.

15. The trough of claim 14, wherein one of said first and second sealing means comprises a means to conform to the top of the plate and to the top frame portion.

16. The trough of claim 15, wherein one of said first and second sealing means comprises a perfluoroelastomeric material.

17. The trough of claim 16, wherein said perfluoroelastomeric material is shaped as an O-ring.

18. The trough of claim 16, wherein the other of said first and second sealing means comprises a fluorocarbon resin.

19. The trough of claim 14, wherein said first and second sealing means are respectively selected from a group consisting of perfluorelastomers and fluorcarbon resins.

20. The trough of claim 14, further comprising a stop atached to said frame, formed and positioned to engage with said moveable barrier.

21. The trough of claim 14, wherein said securing means comprises:
   a pair of threaded mating portions respectively on said top and bottom frame portions; and
   one of said first and second sealing means comprises a means to conform to the top of the plate and to the top frame portion.

22. The trough of claim 16, wherein said securing means comprises:
   a pair of threaded mating portions respectively on said top and bottom frame portions; and
   said one of said first and second sealing means comprises a means to conform to the top of the plate and to the top frame portion.

23. The trough of claim 14, wherein said frame has at least one port positioned to communicate with the interior of said frame below said organic film and dimensioned to receive a syringe.

24. The trough of claim 23, additionally comprising a syringe housing removably connected to said port.

25. The trough of claim 14, wherein said barrier is formed from a perfluoroelastomer.

26. The trough of claim 14, further including spacer means positioned between the bottom of said plate and the bottom frame portion.

27. The trough of claim 26, wherein said spacer means is selected from a group consisting of perfluoroelastomers and fluorocarbon resins.

28. The trough of claim 14, wherein:
   said plate is annular in shape with an inner radius and an outer radius; and
   said top and bottom frame portions respectively comprise inner-radius and outer-radius frame portions.

29. The trough of claim 28, wherein said plate comprises a chemically-inert and hydrophilic substance.

30. The trough of claim 29, wherein said plate comprises fused silica.

31. The trough of claim 14, wherein the one of the first and second sealing means that is closer to the intended location of the subphase includes an extension in the direction of the subphase, such extension presenting a hydrophobic wall to contact and hold the subphase in place.

32. The trough of claim 16, wherein said perfluoroelastomeric material is cross-linked.

33. A trough for the formation of a monomolecular layer of an organic film on a subphase, comprising:
   a frame having top and bottom separable frame portions;
   a plate disposed within said frame and formed of a rigid substance;
   sealing means of chemically inert material positioned between the top of said plate and the top frame portion and comprising a perfluoroelastomeric material that is conformable to the top of the plate and to the top frame portion to prevent subphase leakage from said trough material; and
   means for laterally compressing a layer of amphipilic solution deposited on said subphase to form a solid monomolecular film, said means including a movable barrier dimensioned to rest in superposed relation on said plate.

34. The trough of claim 33, wherein said sealing means is hydrophobic and includes an extension away from said top frame portion and on the plate for holding the subphase in place.

35. The trough of claim 33, further comprising a stop atached to said frame, formed and positioned to engage with said moveable barrier.

36. The trough of claim 33, wherein said securing means comprises a pair of threaded mating portions respectively on said top and bottom frame portions.

37. The trough of claim 33, wherein said frame has at least one port positioned to communicate with the interior of said frame below said organic film and dimensioned to receive a syringe.

38. The trough of claim 37, additionally comprising a syringe housing removably connected to said port.

39. The trough of claim 33, wherein said barrier is formed from a perfluoroelastomer.

40. The trough of claim 33, further including spacer means positioned between the bottom of said plate and the bottom frame portion.

41. The trough of claim 40, wherein said spacer means is selected from a group consisting of perfluoroelastomers and fluorocarbon resins.

42. The trough of claim 33, wherein:
   said plate is annular in shape with an inner radius and an outer radius; and
   said top and bottom frame portions respectively comprise inner-radius and outer-radius frame portions.

43. The trough of claim 33, wherein said plate comprises a chemically-inert and hydrophilic substance.

44. The trough of claim 43, wherein said plate comprises fused silica.

45. The trough of claim 33, wherein said perfluoroelastomeric material is cross-linked.

* * * * *